United States Patent [19]

Ledent et al.

[11] Patent Number: 4,477,390

[45] Date of Patent: Oct. 16, 1984

[54] AMINOMETHYLENEPHOSPHONIC ACID SOLUTIONS

[75] Inventors: Michel A. O. Ledent, Namur; Bronislav H. May, Overijse, both of Belgium

[73] Assignee: Monsanto Company, St. Louis, Mo.

[21] Appl. No.: 294,872

[22] Filed: Aug. 21, 1981

[51] Int. Cl.$^3$ .............................................. C07F 9/38
[52] U.S. Cl. ............................................ 260/502.5 E
[58] Field of Search ...................................... 260/502.5

[56] References Cited

U.S. PATENT DOCUMENTS 3,974,090  8/1976  Mitchell ........................... 260/502.5

OTHER PUBLICATIONS

Van Wazer, "Phosphorus and its Compounds" vol. 1, 1958, pp. 379, 380.

Primary Examiner—J. E. Evans
Attorney, Agent, or Firm—Jon H. Beusen; James C. Logomasini; Arnold H. Cole

[57] ABSTRACT

Aqueous solutions of aminomethylenephosphonic acid selected from diethylenetriaminepenta(methylenephosphonic acid). diethylenetriaminetetra(methylenephosphonic acid), diethylenetriaminetri(methylenephosphonic acid) and mixtures thereof are stabilized against crystallization of said aminomethylenephosphonic acid by including non-oxidizing mineral acid in such solutions in an amount stoichiometrically equivalent to at least 10% hydrochloric acid by weight of the solution.

16 Claims, No Drawings

AMINOMETHYLENEPHOSPHONIC ACID SOLUTIONS

BACKGROUND OF THE INVENTION

This invention relates to aqueous solutions of aminomethylenephosphonic acid (hereinafter referred to as "AMP acid") selected from diethylenetriaminepenta(methylenephosphonic acid), diethylenetriaminetetra(methylenephosphonic acid) and diethylenetriaminetri(methylenephosphonic acid) (hereinafter designated "D5A", "D4A" and "D3A" respectively), having improved storage stability. The aminomethylenephosphonic acids are useful as sequestrants for metal ions.

Aqueous solutions of AMP acid are existing commercial products, and these usually contain a mixture of D5A, D4A and D3A, of which the principal component, providing at least 40%, e.g. from 55% to 85% and usually from 60% to 80%, of the total weight of D5A, D4A and D3A, is D5A. The remainder is normally mostly D3A together with a small amount of D4A. Other phosphonic acids, e.g. hydroxymethylenephosphonic acid, may be present in trace amounts. Typical commercial products alco contain small amounts of phosphorous acid and hydrochloric acid (HCl), the latter in an amount less than 10% by weight, usually not more than 9%, by weight of the solution. (In the present description and claims, all percentages are by weight, i.e., grams per 100 grams of solution.)

Conventionally, the commercial aqueous solutions are described in terms of their concentration of "active phosphonic acid" which is measured by titrating the phosphonic acid groups in such solutions and converting the results, using predetermined constants, to the stoichiometrically equivalent concentration of D5A. The concentration of AMP acid, expressed in this way as active phosphonic acid, is normally from about 90% to about 99% and most commonly from about 94% to about 98% of the actual concentration of AMP acid.

To minimize handling and transportation costs, it is preferred to ship and store the AMP acid in relatively concentrated solutions, which typically contain from 40% to 55% of active phosphonic acid. A problem with such solutions, (although the problem also exists with more dilute solutions), is a tendency for the AMP acid to crystallize, particularly if the solutions are subjected to sudden changes in environment within a storage temperature range which would be normally from about $-5°$ C. to about 40° C., (most usually 5°-35° C.) but which exceptionally may be as low as about $-20°$ C. or as high as about 50° C.

It might be supposed that solubility of the AMP acid would be suppressed by the common ion effect of the hydrochloric acid in the solution, and that a reduction in the concentration of the HCl might provide an improvement. Alternatively it might be supposed that an increase in the concentration of HCl in the solution, or the addition of some other mineral acid to the solution, might aggravate the problem. In fact, this result is obtained in the case of other aminopolymethylenephosphonic acids such as, e.g. nitrilotri(methylenephosphonic acid) as the limit of its solubility in aqueous solutions at ordinary temperatures (e.g. 25° C.) is driven to very low levels by the presence of HCl in concentrations above 10% of such solutions.

Surprisingly, it has been found that solutions of AMP acid do not show the behavior which would be expected from such considerations, and that solutions containing higher concentrations of HCl than the usual solutions referred to above, i.e., solutions containing 10% or more of hydrochloric acid, have improved stabilities. Other mineral acids have been found to have a similar effect.

Accordingly, the present invention provides aqueous solutions of AMP acid having improved stability against crystallization of the AMP acid, and a method for stabilizing aqueous solutions of AMP acid against such crystallization.

SUMMARY OF THE INVENTION

An aqueous solution of the invention comprises an AMP acid selected from D5A, D4A, D3A and mixtures thereof, and a non-oxidizing mineral acid, the non-oxidizing mineral acid being present in an amount sufficient to inhibit crystallization of AMP acid from the solution, said sufficient amount being an amount of HCl which is at least 10% by weight of the solution or an equivalent amount of at least one other non-oxidizing mineral acid or of a mixture of HCl with at least one other non-oxidizing mineral acid.

This amount of acid is equivalent to about 0.27 gram equivalents of non-oxidizing mineral acid per 100 grams of solution, the gram equivalent of an acid being the weight in grams of the acid which contains one gram of replaceable hydrogen. Irrespective of what may be the actual degree of ionization of the mineral acid in a solution of the invention, the gram equivalent weight of HCl is understood as being the same as its gram molecular weight, the gram equivalent weight of sulfuric acid is understood as being half its gram molecular weight, the gram equivalent weight of phosphoric acid is understood as being one-third its gram molecular weight, and so on.

The method of the invention is a method of stabilizing an aqueous solution of an AMP acid selected from D5A, D4A, D3A and mixtures thereof against crystallization of the AMP acid, which comprises adding non-oxidizing mineral acid to an aqueous solution of the AMP acid to provide an amount of non-oxidizing mineral acid in the solution sufficient to inhibit crystallization of AMP acid therefrom, the said amount being defined above.

DETAILED DESCRIPTION OF THE INVENTION

As used herein, the term "non-oxidizing mineral acid" refers to a mineral acid which does not significantly oxidize D5A, D4A or D3A in an aqueous solution at 25° C. The most preferred of these is HCl but others, e.g. sulfuric, phosphoric, phosphorous, or hydrobromic, as well as mixtures of two or more of such mineral acids may be used satisfactorily.

The mineral acid can be added to the solution by any suitable procedure. E.g., when such a mineral acid is present, following the reaction employed in production of the AMP acid, in an amount insufficient for good stabilization of an aqueous solution containing the AMP acid product, more of that mineral acid and/or other such mineral acids may be subsequently added to reach the total amount required for such stabilization.

It is often convenient to add the extra mineral acid in the form of an aqueous solution of the acid, e.g. HCl as a 32% aqueous solution or sulfuric acid as a 50% aqueous solution.

Such a procedure involves the addition of water as well as acid, and for the production of concentrated AMP acid solutions, the evaporation of at least an equivalent amount of water from the original AMP acid solution prior to the addition of the mineral acid solution is a preferred procedure.

The invention has its principal application in the stabilization of commercial solutions of AMP acid in concentrated or diluted form, in which, as indicated above, AMP acid is present as mixtures of D5A, D4A and D3A. In practice, the solutions will usually contain at least about 10% of active phosphonic acid, but not more than about 60% and more usually not more than about 55% of active phosphonic acid. The temperatures at which such solutions are stabilized in accordance with this invention are those mentioned hereinbefore, i.e., from about $-20°$ to about $50°$ C., more importantly from about $-5°$ to about $40°$ C., and most importantly from about $5°$ to about $35°$ C.

The minimum and optimum amounts of non-oxidizing mineral acid normally required for good stabilization vary with the particular mineral acid or mixture of mineral acids used, and with the concentration of AMP acid. There may also be some variation from batch to batch of commercial AMP acid due possibly to slight variations in the proportions of D5A, D4A and D3A in the mixture and in the amounts of impurities present.

The preferred mineral acid in the solutions of the invention is HCl. When this is used as the sole non-oxidizing mineral acid, the stabilization of solutions containing up to about 45% of AMP acid usually requires the presence of at least 14.8%, and preferably at least 15% of HCl; the optimum concentration of HCl is usually in the range 15 to 20%, and often in the range 15 to 17%.

Variations in the minimum amount of HCl required for stabilization of different batches of AMP acid of approximately the same active phosphonic acid content are most apparent with solutions containing about 50%, for example from about 48% to about 51% active phosphonic acid (which typically corresponds to about 50 to 53% of AMP acid). It is usually found that a concentration of at least about 11.5%, e.g. 12–13% HCl is required, and for some batches the necessary minimum concentration of HCl may be higher, for example 14% or 15%.

At AMP acid concentrations above about 50%, the minimum concentration of HCl required for stabilization is usually at least about 11.5% and more usually 12–13%.

For all these solutions, the concentration of HCl in practice will normally not exceed about 20%, and is preferably not greater than about 17%, although higher concentrations are within the scope of the invention.

When mixtures of sulphuric acid and HCl are employed, stabilization usually requires the presence of at least 0.40 total gram equivalents of mineral acid per 100 grams of solution. However, concentrations of mixed acid as low as this figure, or even as low as 0.45 total gram equivalents per 100 grams of solution, are in general effective only in concentrated solutions containing about 45% or more AMP acid. Solutions that are more dilute with respect to AMP acid require a higher minimum combined HCl/H$_2$SO$_4$ content for their stabilization. At about 30% AMP acid, the minimum is usually about 0.5 total gram equivalents of mineral acid per 100 grams of solution. Thus, for solutions containing about 30% or more of AMP acid, a preferred total gram equivalents of HCl/H$_2$SO$_4$ per 100 grams of solution is from about 0.41 to about 0.55. At about 10% of AMP acid, the minimum combined HCl/H$_2$SO$_4$ content required for stabilization is usually about 0.6 total gram equivalent of mineral acid per 100 grams of solution.

The relative proportions of HCl and H$_2$SO$_4$ in a mixture of HCl and H$_2$SO$_4$ used to stabilize AMP acid solutions in accordance with the invention may also be a further factor in determining the minimum total mineral acid concentration required. There are indications that the minimum will decrease as the proportion of HCl in the mixture (on a gram equivalent basis) increases.

In practice, the mineral acid content of solutions stabilized with mixtures of HCl and H$_2$SO$_4$ will normally not exceed the required minimum by more than about 0.2 gram equivalents of total mineral acid per 100 grams of solution, but larger amounts than this, e.g. up to about 0.9 gram equivalents per 100 grams of solution, may be present.

Stabilization by the addition of phosphoric or phosphorous acids to a solution of AMP acid containing about 5% or less of HCl requires the use of relatively large amounts of H$_3$PO$_4$ or H$_3$PO$_3$. E.g., as shown by the data set out in the tables below, the stable solutions are those that contain at least about 30% by weight of H$_3$PO$_4$ or at least about 40% by weight of H$_3$PO$_3$.

It will be appreciated that, because of the number of variables in the system, to specify minimum and optimum amounts of stabilizing mineral acid for all conceivable combinations of variables is impossible. However, the procedure for assessing solution stability as set out below is straightforward, and its performance in order to determine the amounts of mineral acid required to achieve the object of the invention in any particular instance is well within the capability of the person skilled in the art.

As a generality, however, solutions containing at least about 30% of active phosphonic acid will usually be stable provided they contain more than 0.40, e.g. from about 0.41 to about 0.55 gram equivalents of non-oxidizing mineral acid, per 100 grams of solution. In some instances, the minimum concentration of mineral acid required for stability will be towards the upper end of this range. Moreover, solutions containing about 50% or more of active phosphonic acid are in some instances stabilized by the presence of 0.40 gram equivalents of mineral acid or less, provided they contain at least 10%, preferably at least 12% of HCl.

In addition to the aforementioned AMP acid and non-oxidizing mineral acids, the compositions claimed herein can include various other constituents which do not prevent substantial realization of advantages of this invention. E.g., such other constituents may include other metal sequestrants, e.g. other polymethylenephosphonic acids such as nitrilotri(methylenephosphonic acid), ethylenediaminetetra(methylenephosphonic acid), hexamethylenediaminetetra(methylenephosphonic acid) and triethylenetetraminehexa(methylenephosphonic acid).

The invention is illustrated by the following Examples.

EXAMPLES 1–34

Solutions 1–34 containing various concentrations of active phosphonic acid and HCl were prepared by additions of 32% HCl solution or 32% HCl solution and water to samples of a commercially available product which is an aqueous solution containing 6.86% HCl and 50.4% of active phosphonic acid (corresponding to 52% AMP acid of which about 70% is D5A, 28% is D3A and 2% is D4A.

After thorough mixing, each solution was seeded with crystals of pure D5A and stored at 20° C. A solution is regarded as stabilized in accordance with the invention if the seeds dissolve to give a clear solution which remains clear for at least 24 hours after seeding. The observations are shown below.

| Solution No. | % Active Phosphonic Acid Content | Total HCl Content % | Gm.Eqs./ 100 Gms. Soln. | Observations |
|---|---|---|---|---|
| 1 | 35 | 15.6 | 0.43 | Seeds dissolved after 1 minute; solution remained clear on storage. |
| 2 | 35 | 13.8 | 0.38 | Solution slightly turbid. |
| 3 | 35 | 12.0 | 0.33 | Turbid solution after seeding followed by slight precipitation within 3 hours. Precipitate stuck to the bottom. |
| 4 | 35 | 10.2 | 0.28 | Same as Solution No. 3. |
| 5 | 35 | 8.4 | 0.23 | Turbid solution after seeding. Considerable deposits after 2 days storage. |
| 6 | 30 | 18.51 | 0.51 | Seeds dissolved quickly. Clear solution. |
| 7 | 30 | 14.91 | 0.41 | Same as Solution No. 6. |
| 8 | 30 | 11.31 | 0.31 | Turbid solution after seeding. Precipitation on storage. |
| 9 | 30 | 7.71 | 0.21 | Considerable precipitation after 2 days storage. |
| 10 | 30 | 5.91 | 0.16 | Same as Solution No. 9. |
| 11 | 30 | 4.11 | 0.11 | Same as Solution No. 9. |
| 12 | 25 | 21.43 | 0.59 | Seeds dissolved quickly. Clear solution after 2 minutes. |
| 13 | 25 | 17.83 | 0.49 | Same as Solution No. 12. |
| 14 | 25 | 16.03 | 0.44 | Same as Solution No. 12. |
| 15 | 25 | 14.23 | 0.39 | Turbid solution after seeding. Very slight sedimentation on storage. |
| 16 | 25 | 10.63 | 0.29 | Precipitation on storage. |
| 17 | 20 | 24.34 | 0.67 | Clear solution after seeding. Solution remained stable on storage. |
| 18 | 20 | 20.74 | 0.57 | Clear solution after seeding. Stable solution. |
| 19 | 20 | 17.14 | 0.47 | Seeds dissolved quickly. Clear solution on storage. |
| 20 | 20 | 15.34 | 0.42 | Same as Solution No. 19. |
| 21 | 20 | 13.54 | 0.37 | Cloudy solution after seeding. Slight sedimentation after 3 days. |
| 22 | 20 | 9.94 | 0.27 | Non-stable solution. Precipitation after seeding. |
| 23 | 15 | 27.26 | 0.75 | Stable clear solution. |
| 24 | 15 | 23.7 | 0.65 | Stable clear solution. |
| 25 | 15 | 20.0 | 0.55 | Stable clear solution. |
| 26 | 15 | 16.46 | 0.45 | Stable clear solution. |
| 27 | 15 | 14.6 | 0.40 | Cloudy solution on mixing. Very slight sedimentation. |
| 28 | 15 | 12.86 | 0.35 | Cloudy solution. Slight sedimentation. |
| 29 | 10 | 30.17 | 0.83 | Stable clear solution. |
| 30 | 10 | 26.6 | 0.73 | Stable clear solution. |
| 31 | 10 | 23.0 | 0.63 | Stable clear solution. |
| 32 | 0 | 19.37 | 0.53 | Stable clear solution. |
| 33 | 0 | 15.77 | 0.43 | Stable clear solution. |
| 34 | 10 | 12.17 | 0.33 | Cloudy solution on mixing. Sedimentation on storage. |

From the data above it can be seen that stable solutions are obtained if the total HCl content is greater than 0.40 gram equivalents per 100 grams of solution, and that this minimum mineral acid concentration is required irrespective of the concentration of active phosphonic acid over the range 10%–35% active phosphonic acid.

EXAMPLES 35–42

To prepare Solutions Nos. 35–42, 98% $H_2SO_4$ was added to solutions containing various concentrations of active phosphonic acid obtained by diluting a commercial product containing 50% of active phosphonic acid (corresponding to about 51.7% AMP acid). After thorough mixing, each solution was seeded with crystals of pure D5A and stored at 20° C. Observations of the stabilities of the solutions are shown in the table.

| Solution No. | % Active Phosphonic Acid Content | Mineral Acid Content % HCl | % $H_2SO_4$ | Total Gm. Eqs./ 100 Gms. Soln. | Observations |
|---|---|---|---|---|---|
| 35 | 30 | 4.44 | 30 | 0.73 | Stable clear solution. |
| 36 | 30 | 4.44 | 20 | 0.53 | Stable clear solution |
| 37 | 30 | 4.44 | 15 | 0.43 | Cloudy solution on mixing; sedimen- |

-continued

| Solution No. | % Active Phosphonic Acid Content | Mineral Acid Content | | Total Gm. Eqs./ 100 Gms. Soln. | Observations |
|---|---|---|---|---|---|
| | | % HCl | % $H_2SO_4$ | | |
| 38 | 30 | 4.44 | 10 | 0.33 | tation on storage. Same as Solution 37. |
| 39 | 10 | 1.47 | 50 | 1.06 | Stable clear solution. |
| 40 | 10 | 1.47 | 30 | 0.65 | Stable clear solution. |
| 41 | 10 | 1.47 | 25 | 0.55 | Slight sedimentation on storage. |
| 42 | 10 | 1.47 | 20 | 0.45 | Cloudy solution on mixing. Precipitation on storage. |

From these results, it can be concluded that to stabilize solutions containing 30% active phosphonic acid and the indicated amount of HCl, the addition of $H_2SO_4$ to give a total mineral acid concentration of about 0.5 gram equivalents per 100 grams of solution is effective in stabilizing the solution. For solutions containing 10% active phosphonic acid, the addition of $H_2SO_4$ to give a total mineral acid content of about 0.6 gram equivalents of acid per 100 grams of solution is effective.

EXAMPLES 43 AND 44

Solutions 43 and 44 were prepared similarly to Solutions 35-42, but using glacial phosphoric acid instead of $H_2SO_4$.

| Solution No. | % Active Phosphonic Acid Content | Mineral Acid Content | | Total Gm. Eqs./ 100 Gms. Soln. | Observations |
|---|---|---|---|---|---|
| | | % HCl | % $H_3PO_4$ | | |
| 43 | 30 | 4.44 | 34.4 | 1.17 | Stable clear solution. |
| 44 | 30 | 4.44 | 20.3 | 0.74 | Cloudy solution on mixing. |

EXAMPLES 45-48

Solutions 45-48 were prepared similarly to Solutions 35-42, but using $H_3PO_3$ instead of $H_2SO_4$.

| Solution No. | % Active Phosphonic Acid Content | Mineral Acid Content | | Total Gm. Eqs./ 100 Gms. Soln. | Observations |
|---|---|---|---|---|---|
| | | % HCl | % $H_3PO_3$ | | |
| 45 | 20 | 3.2 | 42 | 1.63 | Clear solution after seeding. |
| 46 | 10 | 1.6 | 56 | 2.09 | clear solution after seeding. |
| 47 | 10 | 1.6 | 49 | 1.84 | Clear solution after seeding. |
| 48 | 10 | 1.6 | 35 | 1.32 | Cloudy solution on mixing. |

EXAMPLES 49-63

The solutions of these Examples were prepared by concentrating a sample of the commercially available product used in Examples 1-34 to about 70% active acid content, and adding 32% HCl solution, 50% $H_2SO_4$ solution, water or combinations thereof to portions of the concentrated solution. After thorough mixing, each solution was seeded with crystals of pure D5A and stored at 20° C.

| Solution No. | % Active Phosphonic Acid Content | Mineral Acid Content | | Total Gm. Eqs./ 100 Gms. Soln. | Observations |
|---|---|---|---|---|---|
| | | % HCl | % $H_2SO_4$ | | |
| 49 | 50 | 6.44 | 14.79 | 0.48 | Clear |
| 50 | 50 | 5.44 | 9.58 | 0.38 | Cloudy |
| 51 | 50 | 12.5 | 6.34 | 0.47 | Clear |
| 52 | 50 | 12.5 | 2.82 | 0.40 | Clear |
| 53 | 50 | 15.0 | — | 0.41 | Clear |
| 54 | 50 | 12.5 | — | 0.34 | Clear |
| 55 | 50 | 11.0 | — | 0.30 | Cloudy |
| 56 | 50 | 10.0 | — | 0.27 | Precipitate |
| 57 | 52 | 10 | — | 0.27 | Cloudy |
| 58 | 52 | 11 | — | 0.30 | Cloudy |
| 59 | 52 | 12.3 | — | 0.34 | Clear |
| 60 | 55 | 7.08 | 11.24 | 0.42 | Clear |
| 61 | 55 | 12.3 | — | 0.34 | Clear |
| 62 | 57 | 12.4 | — | 0.34 | Clear |
| 63 | 60 | 12 | — | 0.33 | Clear |

Comparison of Examples 49-62 with Examples 35-42 shows that when using mixtures of HCl and $H_2SO_4$, the more concentrated active phosphonic acid Solutions Nos. 49-52 and 60 require less total HCl plus $H_2SO_4$ for stabilization than the more dilute Solutions Nos. 35-42.

We claim:

1. An aqueous solution comprising an aminomethylenephosphonic acid selected from diethylenetriaminepenta(methylenephosphonic acid), diethylenetriaminetetra(methylenephosphonic acid), diethylenetriaminetri(methylenephosphonic acid) and mixtures thereof and a non-oxidizing mineral acid, characterized in that said mineral acid is present in an amount sufficient to inhibit crystallization of said aminomethylenephosphonic acid from the solution, said sufficient amount comprising an amount of hydrochloric acid which is at least about 12% by weight of the solution.

2. A solution according to claim 1 wherein said aminomethylenephosphonic acid is a mixture of diethylenetriaminepenta(methylenephosphonic acid), diethylenetriaminetetra(methylenephosphonic acid) and diethylenetriaminetri(methylenephosphonic acid) containing from about 55% to about 85%, based on the weight of the mixture, of diethylenetriaminepenta(methylenephosphonic acid).

3. A solution according to claim 1, wherein said mineral acid is a mixture of hydrochloric acid and sulfuric acid.

4. A solution according to claim 1 which contains from about 50% to about 60% of said aminomethylenephosphonic acid.

5. A solution according to claim 1 wherein said amount is sufficient to inhibit said crystallization within a temperature range from about −5° to about 40° C.

6. A method for stabilizing an aqueous solution of aminomethylenephosphonic acid selected from diethylenetriaminepenta(methylenephosphonic acid), diethylenetriaminetetra(methylenephosphonic acid), diethylenetriaminetri(methylenephosphonic acid) and mixtures thereof against crystallization of said aminomethylenephosphonic acid, which comprises adding non-oxidizing mineral acid to the solution until the amount of non-oxidizing mineral acid in the stabilized solution is sufficient to inhibit said crystallization, said sufficient amount comprising an amount of hydrochloric acid which is at least about 12% by weight of the solution.

7. A method according to claim 6 in which said aminomethylenephosphonic acid is a mixture of diethylenetriaminepenta(methylenephosphonic acid), diethylenetriaminetetra(methylenephosphonic acid) and diethylenetriaminetri(methylenephosphonic acid) containing from about 55% to about 85%, based on the weight of said mixture, of diethylenetriaminepenta(methylenephosphonic acid).

8. A method according to claim 6 in which the stabilized solution contains from about 30% to about 55% of said aminomethylenephosphonic acid and from about 0.41 to about 0.55 gram equivalents of mineral acid per 100 grams of solution.

9. A method according to claim 6 wherein the stabilized solution contains from about 50% to about 60% of said aminomethylenephosphonic acid.

10. A method according to claim 6 wherein said amount is sufficient to inhibit said crystallization within a temperature range from about −5° to about 40° C.

11. A solution according to claim 1 which contains at least about 30% of active aminomethylenephosphonic acid.

12. A solution according to claim 11 wherein said amount of hydrochloric acid is more than 0.40 gram equivalents per 100 grams of solution.

13. A solution according to claim 11 containing from about 0.41 to about 0.55 gram equivalents of said non-oxidizing mineral acid.

14. A solution according to claim 13 which contains from about 50% to about 60% of said aminomethylenephosphonic acid.

15. A method according to claim 6, said solution containing at least about 30% of active aminomethylenephosphonic acid.

16. A method according to claim 15, said sufficient amount comprising an amount of hydrochloric acid which is at least about 14.8% by weight of the solution.

* * * * *